(12) United States Patent
Herzon (10) Patent No.: US 6,235,027 B1
(45) Date of Patent: *May 22, 2001

(54) THERMAL CAUTERY SURGICAL FORCEPS (76) Inventor: Garrett D. Herzon, 2132 Century Park La., No. 108, Los Angeles, CA (US) 90067

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,229

(22) Filed: Jan. 21, 1999

(51) Int. Cl.[7] .................................................. A61B 18/18
(52) U.S. Cl. .............................. 606/51; 606/28; 606/30; 606/42; 606/49
(58) Field of Search ..................... 606/27, 28, 29, 606/30, 31, 41, 42, 49, 52, 51

(56) References Cited

U.S. PATENT DOCUMENTS

| D. 253,303 | 10/1979 | Barton et al. . | |
|---|---|---|---|
| D. 254,150 | 2/1980 | Barton et al. . | |
| 1,229,704 | * 6/1917 | Berry . | |
| 1,366,231 | * 1/1921 | Winter et al. . | |
| 1,584,444 | * 5/1926 | Flick . | |
| 2,030,285 | * 2/1936 | Dinyer | 219/31 |
| 3,100,489 | * 8/1963 | Bagley | 128/303.17 |
| 3,391,690 | * 7/1968 | Armao | 128/2 |
| 3,613,682 | 10/1971 | Naylor . | |
| 3,662,151 | 5/1972 | Haffey . | |
| 3,978,312 | 8/1976 | Barton et al. . | |
| 3,980,861 | * 9/1976 | Fukunaga | 219/230 |
| 4,449,528 | 5/1984 | Auth et al. . | |
| 4,481,057 | 11/1984 | Beard . | |
| 4,485,810 | 12/1984 | Beard . | |
| 4,523,084 | 6/1985 | Tamura et al. . | |
| 4,549,073 | 10/1985 | Tamura et al. . | |
| 4,563,570 | 1/1986 | Johns . | |
| 4,606,342 | 8/1986 | Zamba et al. . | |
| 4,622,966 | 11/1986 | Beard . | |
| 4,662,068 | * 5/1987 | Polonsky | 30/124 |
| 4,691,703 | 9/1987 | Auth et al. . | |
| 4,708,136 | 11/1987 | Saito . | |
| 4,744,359 | 5/1988 | Hatta et al. . | |
| 5,026,370 | * 6/1991 | Lottick | 606/42 |

(List continued on next page.)

OTHER PUBLICATIONS

Starion Instruments trade publication entitled "Cut and coagulate simultaneously with pure heat," 4 pages.
Brochure entitled: "The Hemostatix Thermal Scalpel"; Smith + Nephew.

*Primary Examiner*—John P. Leubecker
*Assistant Examiner*—Jocelyn Ram
(74) *Attorney, Agent, or Firm*—Oblon, Spivak, McClelland, Maier & Neustadt, P.C.

(57) ABSTRACT

A portable, thermal cauterizing forceps device for use in surgery. The device incorporates a pair of ceramic heater elements mounted within the tips of the tines of a forceps. The forceps is used to grasp tissue or blood vessels and apply heat to effect cauterization. In the case of the first embodiment of the invention, the forceps instrument incorporates a battery and control electronics. The thermal-forceps is of a self-contained wireless, handheld disposable design. In a second embodiment of the invention, the forceps handpiece is connected to an external power source. Both embodiments of the forceps incorporate set of rapidly heating ceramic heater elements that may be composed of silicon nitride. An LED provides the operator feedback as to the operating level of the heaters and/or battery reserve. Enhancements to the second embodiment include a rechargeable power supply, variable control of the heater temperature, as well as a, digital display of the tip temperature.

20 Claims, 7 Drawing Sheets

U.S. PATENT DOCUMENTS

| | | |
|---|---|---|
| 5,122,137 | 6/1992 | Lennox . |
| 5,250,046 * | 10/1993 | Lee .................................................. 606/29 |
| 5,306,287 * | 4/1994 | Becker ............................................. 606/205 |
| 5,352,868 | 10/1994 | Denen et al. . |
| 5,401,273 | 3/1995 | Shippert . |
| 5,443,463 * | 8/1995 | Stern et al. ...................................... 606/51 |
| 5,452,513 * | 9/1995 | Zinnbauer et al. ............................. 30/140 |
| 5,533,618 * | 7/1996 | Pickels, Jr. ...................................... 206/363 |
| 5,556,563 * | 9/1996 | von der Heyde et al. ..................... 219/227 |
| 5,565,122 * | 10/1996 | Zinnbauer et al. .............................. 219/227 |
| 5,688,265 | 11/1997 | Citronowicz . |
| 5,792,137 * | 8/1998 | Carr et al. ........................................ 606/29 |
| 5,792,138 * | 8/1998 | Shipp ................................................ 606/38 |
| 5,797,907 | 8/1998 | Clement . |
| 5,976,132 * | 11/1999 | Morris .............................................. 606/49 |
| 6,024,741 * | 2/2000 | Williamson, IV et al. .................... 606/40 |

* cited by examiner

THERMAL CAUTERY SURGICAL FORCEPS

BACKGROUND OF THE INVENTION

The present invention relates to a handheld, portable thermal-cauterizing forceps including an integrated thermal heating surface disposed at each tip.

There are many surgical cautery devices available for the surgeon to ablate and vaporize tissue. Hot knives and cutting coagulators have been used to make skin incisions. The cautery can also be used in surgery to aid in hemostasis or control bleeding by coagulating blood vessels. Employing various cautery modalities decreases the duration of some surgical procedures by providing the surgeon a rapid method of coagulation without the need for suture ligation of blood vessels encountered during dissection.

Typically, surgical cautery is accomplished by directing a heating process onto tissue. The heat may be generated by either a thermal or electro-surgical process. Most commonly, an electro-surgical process using a radio frequency (RF) is used. The RF units generate heat by using high frequency electrical current and the resistive nature of tissue to produce heat. This technique requires a bulky generator and heavy electrical components to operate. Typically, RF electrocautery units require a power lead cable to the electro-surgical hand instrument and a large surface area grounding pad. More often than not, radio frequency surgical units are bulky expensive units which require a cable connection. Employing RF cauterization in a surgical operation may add significant cost to the procedure because the grounding pad, cable and handpiece must all be either re-sterilized or replaced in the case of disposable use.

A less common method of generating heat for coagulation of tissue is by thermal cautery. Thermal cautery is achieved by electrical heating of a resistive-wire loop or resistive electronic part by applying an electrical voltage. The prior art describes many handheld disposable, hot-wire loop cautery instruments. These devices have severe limitations as to their scope of use in surgery. The heat generated by the handheld battery powered devices is very small with a low heat capacity. The available patented devices are effective for cauterization of only the smallest of blood vessels, such as, vessels in the sclera of the eye. These battery powered hot-wire cautery instruments are not effective for use in cauterization of larger blood vessels encountered in most surgical procedures. A technique employing the electrical over driving of a zener diodes to produce heat has also been described in several patents. This device is primarily for limited endoscopic applications.

SUMMARY OF THE INVENTION

In order to overcome the limitations and disadvantages of the prior art, the present invention provides, in an embodiment, a new and improved hand-held, high energy, portable thermal cautery forceps. More particularly, the new and improved surgical forceps instrument includes an enclosure which houses a battery and electronic control. Active ceramic heaters are provided on the two tips of the operative end of the forceps. In a second embodiment, the thermal forceps may alternatively be powered by an external power source.

The new thermo-cautery forceps device in accordance with an embodiment of the invention provides the surgeon with several significant improvements in the state of the art. A first benefit of the thermal-cautery forceps is that it is cordless and fully portable. In the first embodiment of the invention, no cables or external power supply is necessary. This keeps the operative field clear of wires and cables. The thermal cautery of this invention does not require any grounding pad or foot switches.

A second benefit is the very high heating capacity of the thermal elements of the device. Temperatures of over 1000° C. are easily obtainable. A preferred tip operating range is from 650° to 700° C. This heat capacity and temperature can easily cauterize medium and large blood vessels.

A third benefit provided by the new and improved thermal cautery forceps of the invention is its ability to heat to operating temperature in a very short time period, for example, within about one second. The preferred embodiment uses silicon nitride, ceramic heater elements. These new ceramic heaters exhibit rapid heating and cooling characteristics. Silicon nitride ceramic heaters have been used successfully in other fields outside surgery. To the inventor's knowledge, this is believed to be the first use within the field of surgical thermal coagulation.

In an alternative embodiment, less expensive alumina heaters and ceramic resistors or diodes may be employed in substitution for the silicon nitride ceramic heater elements to provide cost savings. However, such alternative types of heaters may be less preferred because longer times to obtain operating temperatures may be required.

In an embodiment, the preferred power source is a battery rendering the device completely portable. Four lithium metal 3 volt batteries can be utilized as well as dual 9 volt batteries, one for each tine. One preferred battery is TADIRAN® which provide 11.5 volts and are rechargeable. A 12 volt direct current power supply can be utilized as well with a connecting cord or cable.

A fourth advantage provided by the new and improved forceps is the placement of the thermal cautery heater elements at the ends of forceps tines. The unique position of the ceramic heater elements allows tissue and blood vessels to be easily grasped and directly coagulated in a controlled manner. The application of a closing or gripping pressure of the forceps against the tissue or vessel enhances the effectiveness of the coagulation.

A fifth benefit of the forceps device in accordance with the invention is to decrease the cost and enhance the availability of surgical cautery. The first embodiment of the thermal forceps allows for the device to be packaged as a sterile disposable instrument. The instrument can be used in emergency or field operations. The device may be used for hemostasis during outpatient surgical procedures in clinics and in surgery centers, as well as, at emergency scenes Other objects and advantages provided by the present invention will become apparent from the following Detailed Description taken in conjunction with the Drawings, in which:

From the above description it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

DETAILED DESCRIPTION OF THE PREFERRED EMBODIMENT

In accordance with a preferred embodiment of the invention, a new and improved thermocautery surgical forceps comprises a surgical forceps body including a pair of elongate tine members extending from the forceps body to respective free end tip portions spaced from the forceps body. The tine members are mounted to the forceps body in a manner providing resilient compressible movement of the tine members between a normally open position, wherein the tines are disposed in aligned, parallel, spaced-apart relationship, and a squeezed closed position, wherein the tip portions of the tine members are disposed in confronting abutting relationship. Each tine member includes a tissue contact surface 18', 19' defined on an inner facing surface of the tine member adjacent the tip portion. A ceramic heater element is disposed in each tine member so as to effectively heat the tissue contact surface to an elevated tissue cauterizing temperature. The ceramic heater elements are optionally connected to a power source. The tine members may be squeezed together to their squeezed closed position to grippingly, squeezably engage tissue to be cauterized between the tip portions. The tissue contact surfaces on the tines may be heated to a tissue cauterizing temperature to effectively thermocauterize the gripped tissue.

Referring now to FIGS. 1–6, a preferred embodiment of the new and improved thermocautery surgical forceps generally designated by reference numeral 10 is shown. Forceps 10 includes a forceps body or housing 12 for the battery 14 (see FIG. 5) and electrical control components 16. Specialized ceramic heating elements 18, 19 are disposed on the tips 20, 21 of the forceps tines 22, 24. FIGS. 1–6 relate to the first embodiment of the invention, that of a portable unit 10 with an internal battery supply 14. FIGS. 7–11 relate to the second embodiment of the invention, that of a cautery unit 26 configured as a thermal forceps 28 with an external power supply (not shown).

Figure 1:
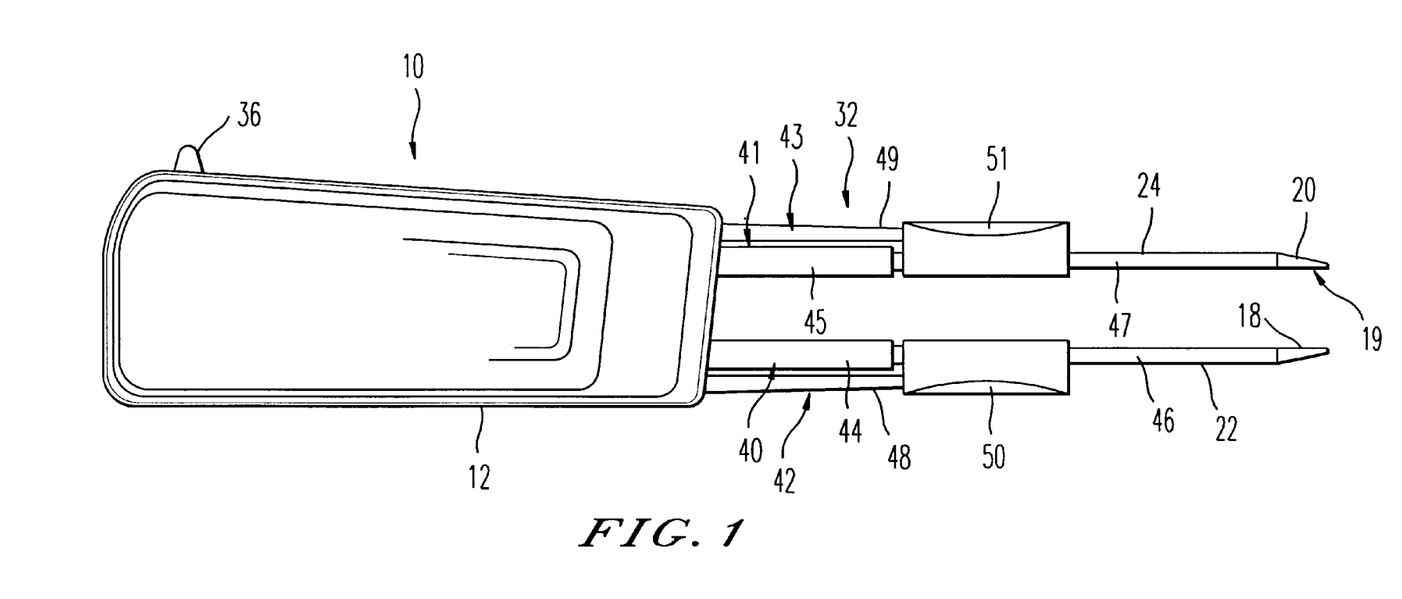
FIG. 1 is a side elevational view of the new and improved thermal cautery forceps instrument of the present invention in accordance with a first embodiment including an internal battery.

As shown in FIG. 1, the first embodiment of the cauterizing instrument 10 generally comprises a housing 12 and an integrated forceps tines assembly 32. The housing 12 encloses the battery 14 (see FIG. 5), and a number of electrical control components 16, such as controller electronics 34, an LED 36 and an internal power switch 38. The forceps tines 22, 24 of the instrument, as shown in FIG. 1, exit from openings in the front end of the housing 12. The forceps assembly comprises two tines 22, 24 of equal length. Each tine 22, 24 is constructed of a heater-carrier 40, 41 and an insulator cover-piece 42, 43. The heater-carriers 40, 41 comprise a metal arm 44, 45 that supports an attached ceramic heater unit 46, 47. Each insulator cover-piece 42, 43 is a shroud 48, 49 that covers the heater 46, 47 and its carrier arm 44, 45. Each shroud cover 48, 49 is heat resistant and protects the surgeon's fingers from the heat generated by the ceramic heaters 46, 47. Each shroud 48, 49 includes a recess 50, 51 to fit the operators thumb and index finger to aid in holding the instrument. Inward compression on the shrouds 48, 49 act to compress the heater carrier arms 44, 45 and will cause the switch 38 (see FIG. 5) to close.

Figure 2:
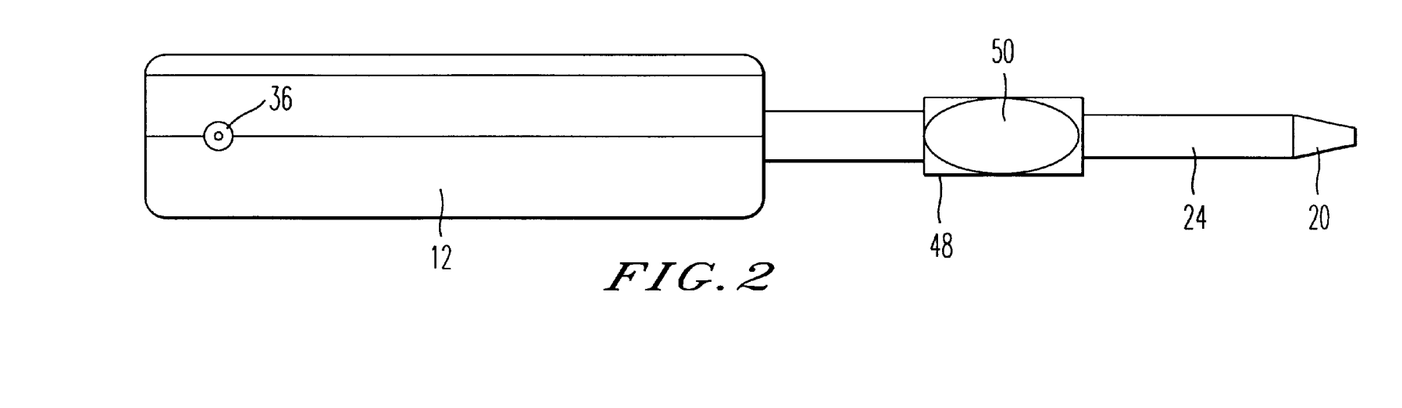
FIG. 2 is a top plan view of the new and improved thermal cautery forceps shown in FIG. 1.
Figure 3:
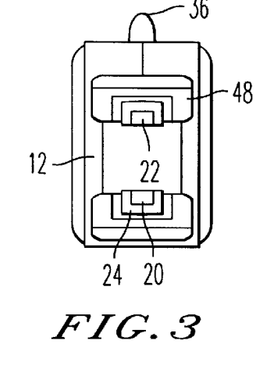
FIG. 3 is an end elevational view of the new and improved thermal cautery forceps showing the front or forceps tines end.
Figure 4:
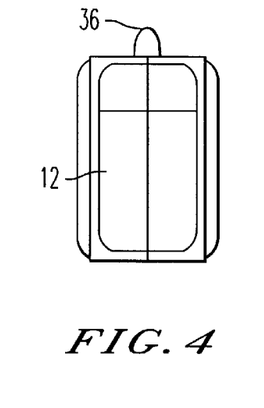
FIG. 4 is an end elevational view of the new and improved thermal cautery forceps viewed from the rear or opposite end of the forceps.

FIG. 2 shows a top view of the instruments with the LED 36 exiting the rear of the housing enclosure and the forceps shroud cover with finger recess The enclosure is rectangular in shape having a closed end and an open end The open end allows the forceps assembly to exit from the enclosure. The enclosure is composed of a plastic formed with an injection process. The open end of the enclosure is shown in FIG. 3. The forceps are shown as well as the LED 36 on the top of the housing. The position of the LED 36 allows the surgeon easily visualize the operation of the instrument. The surgeon can see the LED 36 while it is held in the hand and operated. FIG. 4 shows the closed end of the housing.

Figure 5:
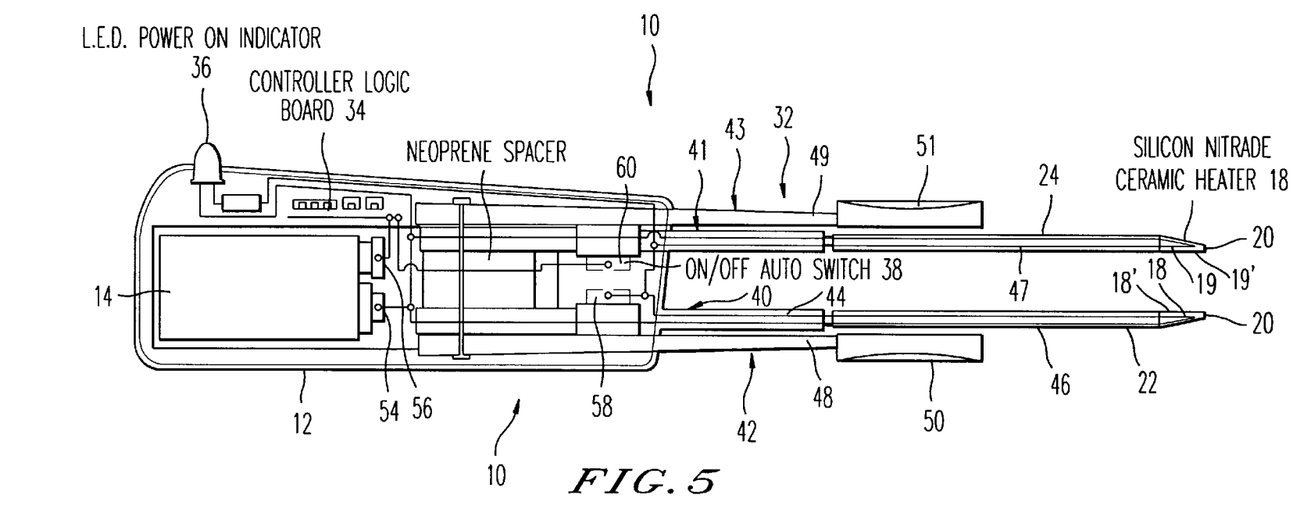
FIG. 5 is an elevated cross-sectional view of the new and improved thermal cautery forceps shown in FIGS. 1–4, showing the logic controller board, LED indicator lamp, internal switch and internal battery.

Shown in FIG. 5 is a cross-sectional view of the enclosure containing a battery 14 for power supply. The battery may be rated form 3 volts to 24 VDC depending on the heating characteristics required. The battery 14 may be of an alkaline or lithium cell. In addition, two 9 volt batteries may be used, one for each tine 22, 24. Lithium metal batteries may also be utilized. One preferred battery is sold under the trademark TADIRAN®. The battery positive and negative terminals 54, 56 are connected to the instrument circuitry by a terminal battery clip. Also, contained within the enclosure is a small circuit board 34 that is populated with an integrated circuit and support components. The circuit board 34 has connections to the power supply 14, LED 36, heater elements 118, 19 and switch mechanism 38. This circuit board 34 acts as a logic-controller to regulate the current delivered to the heating elements. The logic-controller circuit monitors the temperature and resistance of the heater elements 18, 19 and regulates the voltage supply. At the onset of operation the logic circuit allows high current to flow to the heaters 18, 19 aiding in initial rapid heating. The current is then reduced to maintain the heaters 18, 19 at a set temperature. The controller circuit logic also controls the LED 36 to indicate the operative state of the heater elements 18, 19. The LED 36 will illuminate only if the battery power reserve or supply voltage attain a specified level and heaters reach the preset operational temperature. The logic controller also measures the internal resistance and temperature of the heater elements 18, 19. The LED 36 will fail to illuminate if these values fall outside the normal operational limits.

In an alternative design of the first embodiment a small piezo-electric speaker may be incorporated into the forceps enclosure. In the alternative design (not shown) the logic controller is further able to supply a piezo-electric speaker with supply voltage. The piezo-electric speaker provides the operator with auditory feedback pertaining to the operation of the instrument. The speaker emits a sound to give the surgeon an audio feedback as to the operation of the instrument. The sound indicates that the heating elements 18, 19 are at the normal operative temperature for effective cauterization.

Also shown in FIG. 5, is the mounting arrangement of the forceps tines 22, 24. Each tine 22, 24 is mounted on opposite sides of a rectangular neoprene spacer 52. The pair of tines 22, 24 and neoprene spacer 52 are fasted together by a binding pin 54 with end caps. The off-center arrangement fastening of the tines 22, 24 to the neoprene spacer 52 allows for a spring like tweezer effect.

An electrical open/close single pole switch 38 is incorporated into the instrument. The switch 38 is positioned within the housing enclosure 12 between the base of the forceps tines 22, 24. The switch 38 is composed of two contacts 58, 60 that are brought into contact when the forceps 10 are squeezed together. Closing the switch 38 allows current to be delivered to the heaters. The contacts 58, 60 meet, as soon as, closure of the tines 22, 24 is begun and stays in a closed position as long as the tines 22, 24 are closed. Release of the forceps tines 22, 24 will open the switch 38 and current supply to the heaters 46, 47 will terminate.

Figure 6:
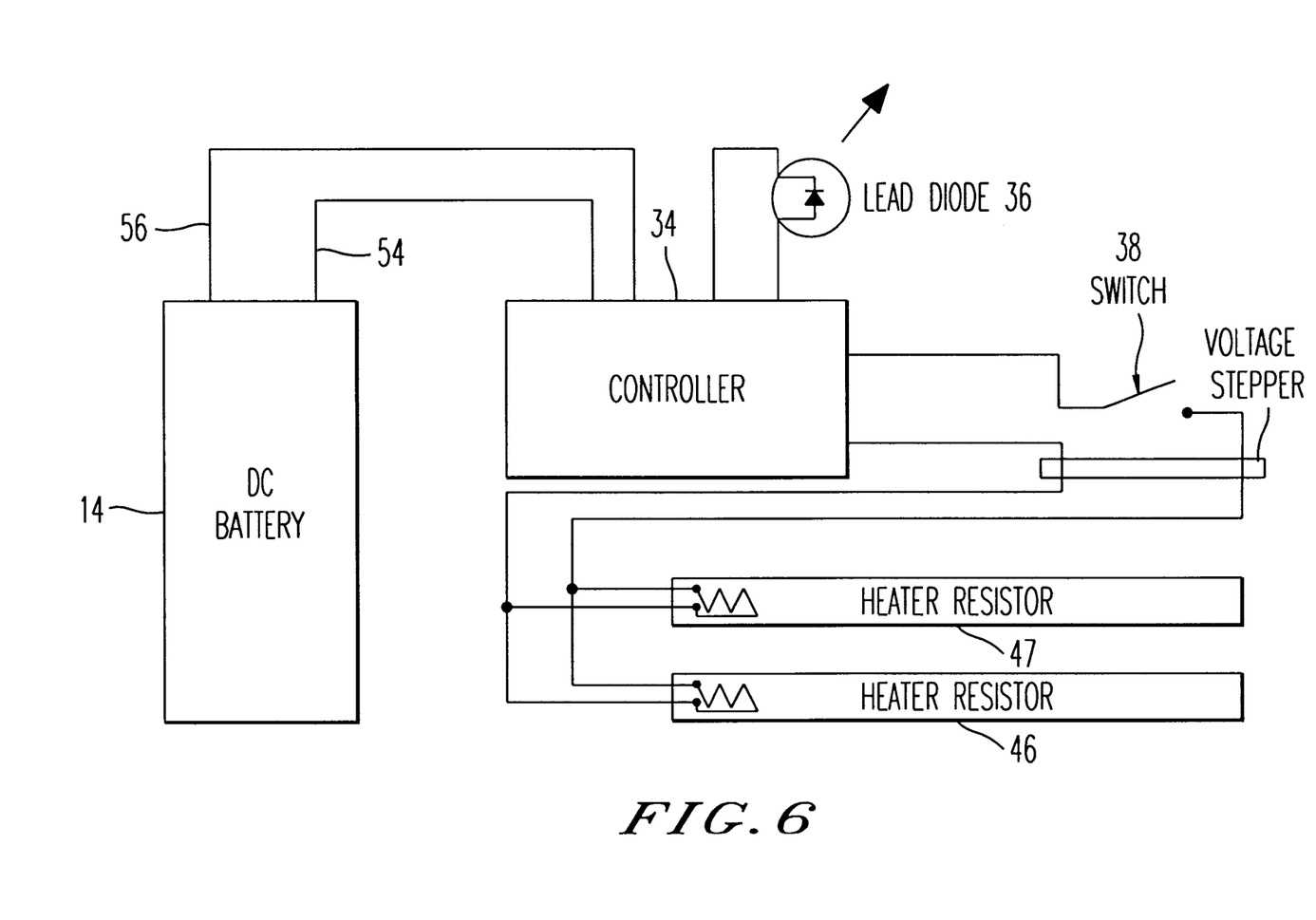
FIG. 6 is a schematic block diagram of the electrical circuit for the new and improved thermal cautery forceps of the first embodiment of the invention comprising a battery powered portable device.
Figure 7:
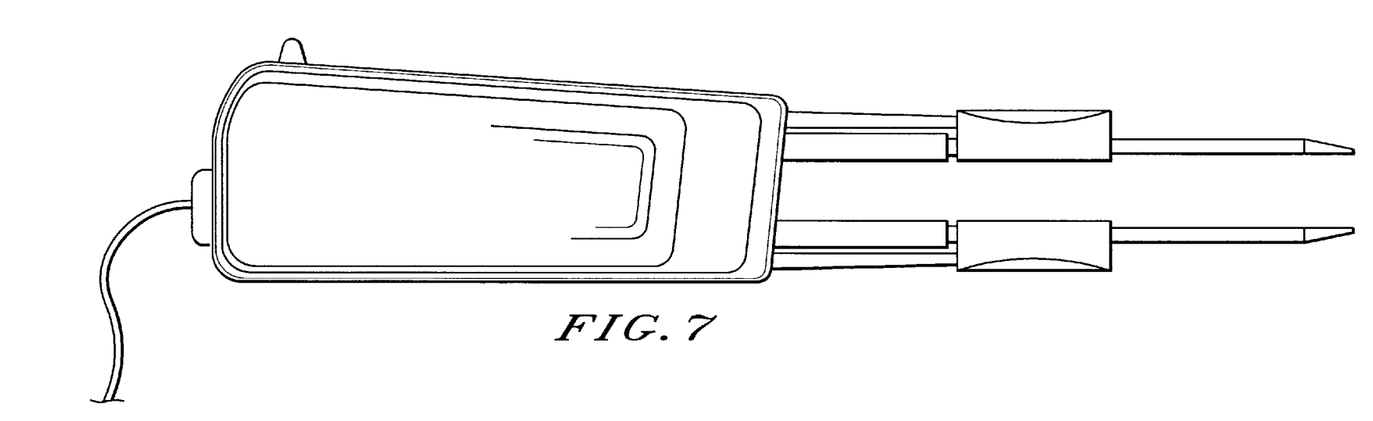
FIG. 7 is an elevated side view of the thermal cautery forceps instrument in accordance with a second embodiment of the invention including an external power supply unit.
Figure 8:
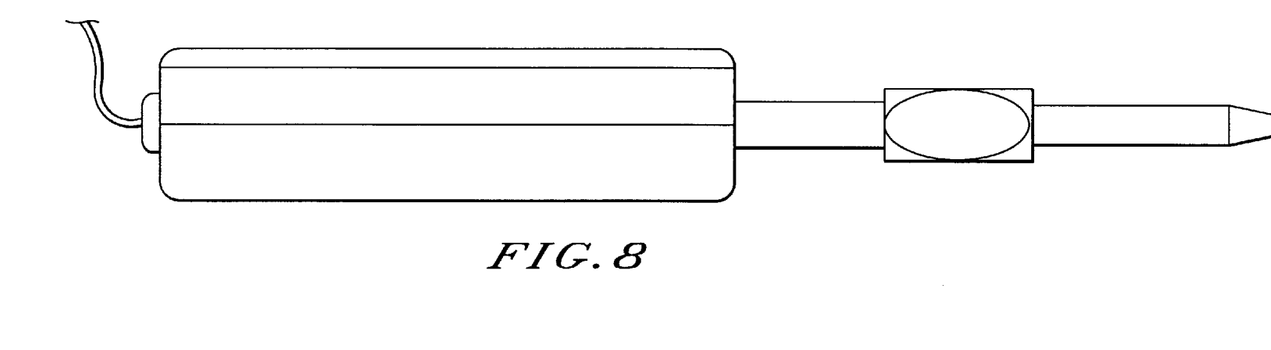
FIG. 8 is a top plan view of the new and improved thermal cautery forceps shown in FIG. 7.
Figure 9:
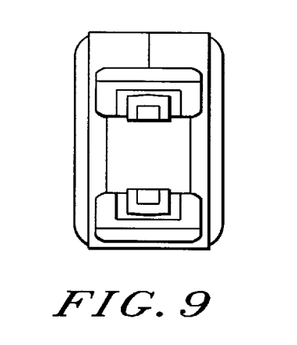
FIG. 9 is an elevated end view of the new and improved thermal cautery forceps of FIG. 7 taken from the forceps tine end.
Figure 10:
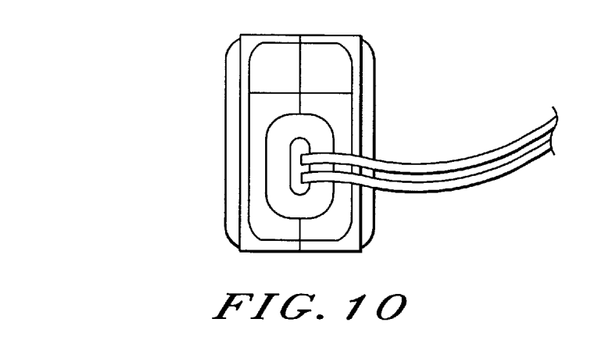
FIG. 10 is an elevated end view of the new and improved thermal cautery forceps shown in FIG. 7, taken from the opposite end and showing the cable connector.
Figure 11:
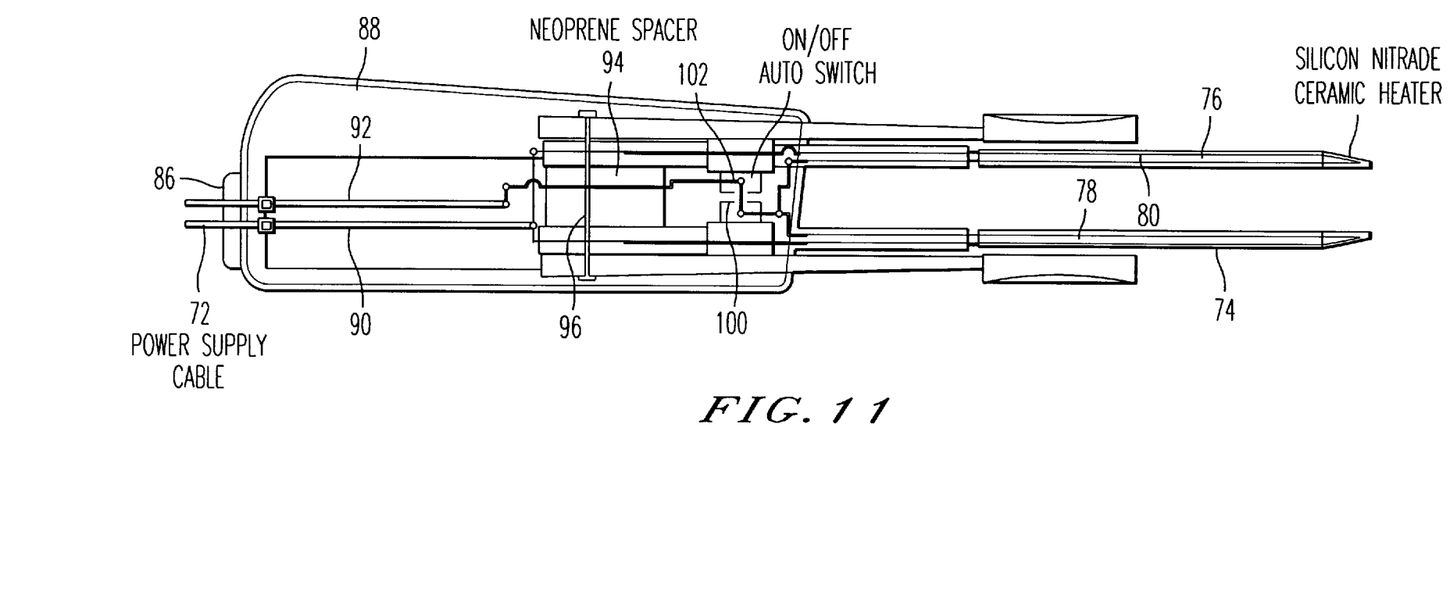
FIG. 11 is an elevated cross-sectional view of the new and improved thermal cautery forceps in accordance with the second embodiment, showing the housing and cable connection to the pair of heater units.

The typical wiring diagram and schematic is shown in FIG. 6. The schematic shows a DC battery 14 with positive and negative leads 54, 56 connected to the logic control circuit board 34. The circuit board 34 is able to regulate the current delivered to the heater elements 46, 47 by measuring the internal electrical resistance of the heaters 46, 47 and the voltage available from the battery 14. The controller also will vary the initial resistance of the heater circuit to obtain quick heat up at power on. The controller logic also controls the illumination of the LED 36. The LED 36 is illuminated when a preset temperature of the heaters 46, 47 is reached. The ON/OFF switch 38 incorporated into the forceps 10 is also depicted. The switch 38 that is closed upon closure of the forceps 10 allows current to flow to the heaters 46, 47. Two heaters 46, 47 are shown which are wired in parallel. The internal resistance of the two heaters 46, 47 is about 5 to 10 ohms, preferably about 8 ohms, or 4 ohms per heater 46, 47. The typical heater 46, 47 is composed of either alumina of silicon nitride or similar glass or ceramic material. This material specification is used due to high wattage density, rapid heat increase to 1000 degrees within one second, high level of insulation and non-stick nature of the ceramic to charred tissue. The preferred tip operating temperature range is 650 to 700° F. The second embodiment 26 of the invention is shown in FIGS. 7–12. In this embodiment an external power source is used to power and control a simple thermal cautery forceps. The forceps 26 in this embodiment is either of an inexpensive disposable or a more durable reusable design. FIGS. 7, 8, 10 and 11 show the externally powered cautery forceps 28. FIG. 7 is a side elevational view of the thermal cautery forceps 28 instrument of the second embodiment of the invention. A cable 72 connects the forceps to the external power supply unit (not shown). Each tine 74, 76 is composed of a rigid metal carrier with ceramic heater 78, 80 and an insulating plastic shroud 82, 84. FIG. 8 is a top plan view thereof; FIG. 9 is an end elevational view there of illustrating the forceps tine end. FIG. 10 is an end elevational view of the end opposite the forceps illustrating the cable connector 86. FIG. 11 is a cross-sectional view of the second embodiment of the present invention, showing the housing 88 and cable connection. A pair of wires 90, 92 connects the cable 72 to the pair of thermal heater elements 78, 80 wired in parallel. Also shown in FIG. 11 is the neoprene spacer 94. The spacer 94 is positioned between the forceps tines 74, 76. An off center-binding pin 96 extends through the tines 74, 76 and the spacer 94 provides a spring effect. The spring effect also activates the ON/OFF switch 98. The switch 98 is composed of two electrical metal contacts 100, 102 affixed to the inside of each forceps tine 74, 76.

Figure 12:
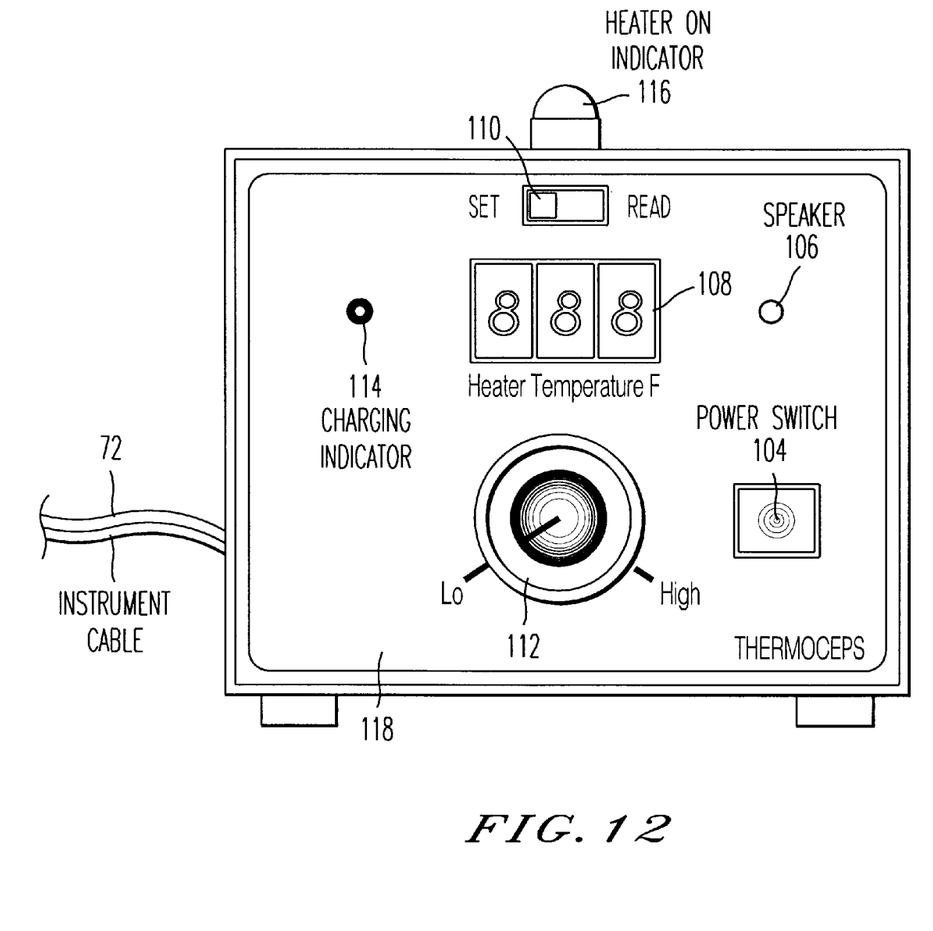
FIG. 12 is an elevated front view of the external power supply unit for use with the new and improved thermal cautery forceps in accordance with the second embodiment showing control features, including a power switch, audio speaker, temperature display, SET/READ switch, temperature control knob, recharging lamp and ready LED lamp.

FIG. 12 is a front elevation of the external power supply unit 103. This unit 103 contains a power switch 104, audio speaker 106, digital temperature display 108, SET/READ switch 110, temperature control knob 112, recharging indicator lamp 114 and ready LED lamp 116. The power supply unit 103 may be a 12 volt DC unit.

As shown in FIG. 12, the cable 72 connected to the forceps 26 enters the power unit 103. The power switch 104 is located on the front panel 118 that illuminates when switch 104 is on. The speaker 106 signals the surgeon of proper heater element temperature for cauterization. The speaker 106 will sound when the instrument reaches the SET temperature after the forceps are squeezed together to initiate heating. The output of the speaker 106 is vented outside the power unit through a small port shown in FIG. 12. The unit also contains a temperature control. The temperature may be varied by positioning the SET/READ switch 110 to the SET position and rotating the temperature adjust knob 112 to the desired temperature. The digital temperature display 108 reports the desired set temperature in degrees fahrenheit. The temperature adjust control 112 may either be of an analogue or digital type. This control allows the surgeon to select a temperature for a desired effect depending on the thickness and moisture content of the tissue to be cauterized. The digital temperature display 108 may indicate the actual temperature of the ceramic heater elements 78, 80 when the SET/READ switch 110 is positioned in the READ position. The LED indicator 114 is incorporated into the power supply, which is illuminated when the batteries are recharging. The Heater On Indicator 116 is incorparated into the power supply, which is illuminated when the heater elements are heated. This occurs whenever the power unit is connected to a 110 VAC line. A charging circuit (not shown) regulates the recharging process.

Figure 13:
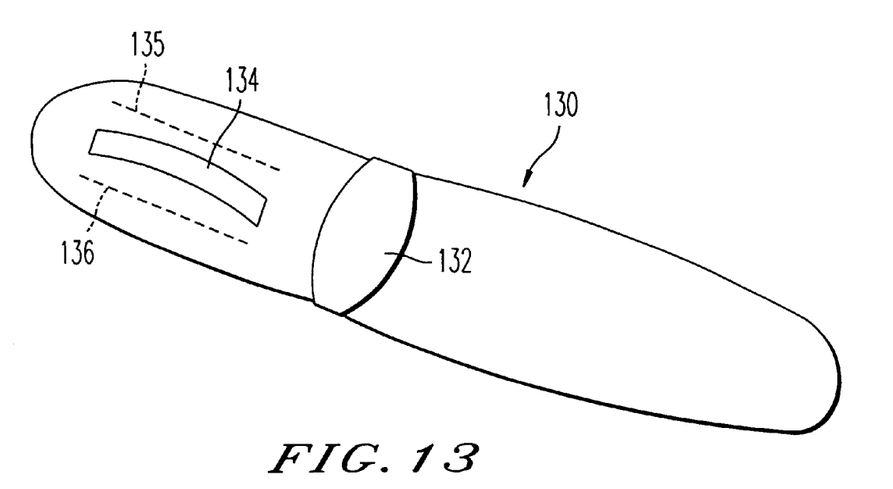
FIG. 13 is a perspective view of a holster for carrying a portable thermal cautery forceps made in accordance with the present invention.
Figure 14:
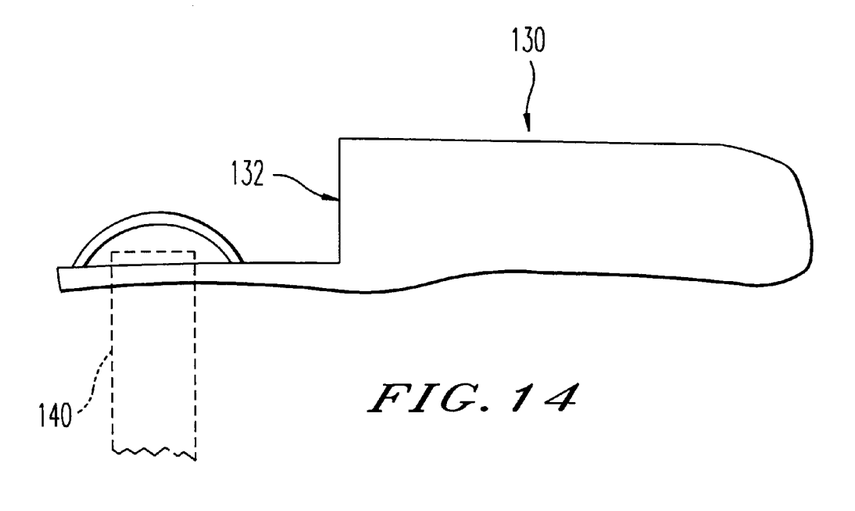
FIG. 14 is a side elevational view of the holster shown in FIG. 13.

FIGS. 13 and 14 illustrate a holster 130 for accommodating the forceps 10 or 26. A cavity 132 receives the tine end of the forceps 10 or 26. A loop 134 or slits 136, 138 may be provided for attaching the holster 130 to a belt 140.

The foregoing discussion of the invention has been presented for purposes of illustration and description. Further, the description is not intended to limit the invention to the form disclosed herein. Consequently, variations and modification commensurate with the above teachings, and the skill or knowledge in the relevant art, are within the scope of the present invention. The embodiments described herein above are further intended to explain modes known of practicing the invention and to enable others skilled in the art to utilize the invention in such, or other embodiments and with various modification required by their particular applications or uses of the invention. It is intended that the appended claim be construed to include alternative embodiments to the extent permitted by the prior art.

What is claimed is:

1. A thermocautery surgical forceps comprising:

a surgical forceps body including a pair of elongate tine members extending from the forceps body to respective free end tip portions spaced from the forceps body, the tine members being mounted to the forceps body in a manner providing resilient compressible movement of the tine members between a normally open position wherein the tines are disposed in aligned, parallel, spaced-apart relationship and a squeezed closed position wherein the tip portions of the tine members are disposed in confronting abutting relationship;

said tip portions of the tine members comprising respective ceramic heater elements having opposed flat gripping and heating surfaces defined on inner facing surfaces of resdective portions, the heater elements connected to power source leads; and the tine members capable of being squeezed together toward their squeezed closed position to grippingly, squeezably engage tissue to be cauterized between the flat gripping and heating surfaces of said ceramic heater elements with the flat gripping and heating surfaces applying substantially uniform pressure and heat to the tissue gripped between the flat gripping and heating surfaces.

2. A thermocautery surgical forceps as defined in claim 1, wherein the ceramic heater elements comprise silicon nitride.

3. A thermocautery surgical forceps as defined in claim 1, further including a switch operationally electrically connected to the ceramic heater elements and the power source leads, and which is effective to automatically turn the ceramic heater elements on to heat the tissue contact surfaces to elevated tissue cauterizing temperature as the tines are moved from the normally open position to the squeezed closed position.

4. A thermocautery surgical forceps as defined in claim 1, which is sterilized and intended for one time disposable use.

5. A thermocautery surgical forceps as defined in claim 1, further comprising a rechargeable battery.

6. The forceps according to claim 1, wherein said flat gripping and heating surfaces are non-stick heating surfaces.

7. A method for thermocauterizing tissue, comprising the steps of:

squeezably grippingly engaging tissue to be cauterized between tip portions of a thermocautery surgical forceps including a pair of spaced and opposed tine members each having tip portions, each tip portion including a ceramic heater element with a flat gripping and heating surface; and activating the ceramic heater elements to heat the flat gripping and heating surfaces thereof to tissue cauterizing temperature and thereby applying substantially uniform pressure and heat to a tissue gripped between the gripping and heating surfaces.

8. The forceps according to claim 7, wherein said flat gripping and heating surfaces are non-stick heating surfaces.

9. A thermocautery forceps kit comprising:

a surgical forceps body including a pair of elongate tine members extending from the forceps body to respective free end tip portions spaced from the forceps body, the tine members being mounted to the forceps body in a manner providing resilient compressible movement of the tine members between a normally open position wherein the tines are disposed in aligned, parallel, spaced-apart relationship and a squeezed closed position wherein the tip portions of the tine members are disposed in confronting abutting relationship;

said tip portions of the tine members comprising respective ceramic heater elements having opposed flat gripping and heating surfaces defined on inner facing surfaces of respective tip portions, the heater elements connected to power source leads;

the tine members capable of being squeezed together toward their squeezed closed position to grippingly, squeezably engage tissue to be cauterized between the flat gripping and heating surfaces of said ceramic heater elements with the flat gripping and heating surfaces applying substantially uniform pressure and heat to the tissue gripped between the flat gripping and heating surfaces; and the thermocautery forceps kit further comprising a heat-resistant holster assembly for holding the forceps body.

10. A thermocautery surgical forceps as defined in claim 9, further comprising at least one battery.

11. A thermocautery surgical forceps as defined in claim 10, wherein at least one battery comprises four 3 volt lithium batteries.

12. A thermocautery surgical forceps as defined in claim 10, wherein at least one battery comprises two 9 volt batteries.

13. A thermocautery surgical forceps as defined in claim 10, wherein the battery comprises an 11.5 volt battery.

14. A thermocautery surgical forceps as defined in claim 9, further comprising a 12 volt DC power supply unit that is connected to the forceps via said power source leads.

15. A thermocautery surgical forceps kit as defined in claim 9, further comprising a rechargeable battery.

16. The forceps according to claim 9, wherein said flat gripping and heating surfaces are non-stick heating surfaces.

17. A thermocautery surgical forceps comprising:

a surgical forceps body including a pair of elongate tine members extending from the forceps body to respective free end tip portions spaced from the forceps body, the tine members being mounted to the forceps body in a manner providing resilient compressible movement of the tine members between a normally open position wherein the tines are disposed in aligned, parallel, spaced-apart relationship and a squeezed closed position wherein the tip portions of the tine members are disposed in confronting abutting relationship;

said tip portions of the tine members comprising respective ceramic heater elements having opposed flat gripping and heating surfaces applying substantially uniform pressure and heat to the tissue gripped between the flat gripping and heating surfaces; and the forceps connected to power source leads.

18. A thermocautery surgical forceps as defined in claim 17, further comprising a 110 v AC power supply connected to said power source leads.

19. A thermocautery surgical forceps as defined in claim 17, further comprising a 12 v DC power supply unit connected to said power source leads.

20. The forceps according to claim 17, wherein said flat gripping and heating surfaces are non-stick heating surfaces.

* * * * *